United States Patent [19]

Kaufman

[11] Patent Number: 5,024,665
[45] Date of Patent: Jun. 18, 1991

[54] COMPOSITE CATHETER ASSEMBLY

[75] Inventor: Jerry M. Kaufman, Eatontown, N.J.

[73] Assignee: Hemedix International, Inc., Eatontown, N.J.

[21] Appl. No.: 522,382

[22] Filed: May 11, 1990

Related U.S. Application Data

[63] Continuation of Ser. No. 271,587, Nov. 14, 1988.

[51] Int. Cl.⁵ .............................................. A61M 5/32
[52] U.S. Cl. .................................. 604/179; 604/263; 604/116
[58] Field of Search ................................ 604/174–180, 604/171, 164, 117, 116, 130, 156, 157, 192, 198, 263, 162–163, 165

[56] References Cited

U.S. PATENT DOCUMENTS

| | | | |
|---|---|---|---|
| 2,008,340 | 7/1935 | Salvati et al. | 604/174 |
| 2,402,306 | 6/1946 | Turkel | 604/174 |
| 3,276,632 | 10/1966 | Stanzel | 604/198 X |
| 3,595,230 | 7/1971 | Suyoeka et al. | 604/164 |
| 4,170,993 | 10/1979 | Alvarez | 604/180 |
| 4,711,636 | 12/1987 | Bierman | 604/180 |
| 4,747,831 | 5/1988 | Kulli | 604/110 |
| 4,850,961 | 7/1989 | Wanderer et al. | 604/53 |
| 4,850,977 | 7/1989 | Bayless | 604/198 |
| 4,932,940 | 6/1990 | Walker et al. | 604/110 |
| 4,941,881 | 7/1990 | Masters et al. | 604/162 |
| 4,946,446 | 8/1990 | Vadher | 604/198 |

FOREIGN PATENT DOCUMENTS 1435246  11/1988  U.S.S.R. ............................. 604/164

Primary Examiner—John D. Yasko
Assistant Examiner—Adam J. Cermak
Attorney, Agent, or Firm—Lerner, David, Littenberg, Krumholz & Mentlik

[57] ABSTRACT

A composite catheter assembly for fixing, locating, inserting and accurately securing intravenous catheters having a needle thereon within body fluid conduits has an attachment plate with an elongated opening therein, a barrel having a bore extending inwardly from one open end of the barrel to define a transverse shoulder so that a passage or sized opening can be provided between the bore and the exterior of the barrel at the transverse shoulder end of the bore, a catheter assembly including, a carrier is slidably mounted in the bore of the barrel for movement of the needle on the catheter assembly from a retracted position in the barrel to an extended position into the body fluid conduit, and a retracting assembly is provided which includes, a spring that is compressed when the catheter assembly is moved from the retracted position to the extended position, and an operatively associated locking and latching assembly to hold and releasably lock the catheter assembly in the extended position and when actuated to permit the compressed spring to retract the catheter assembly and withdraw the needle unil it is returned to the retracted position in the barrel.

11 Claims, 3 Drawing Sheets

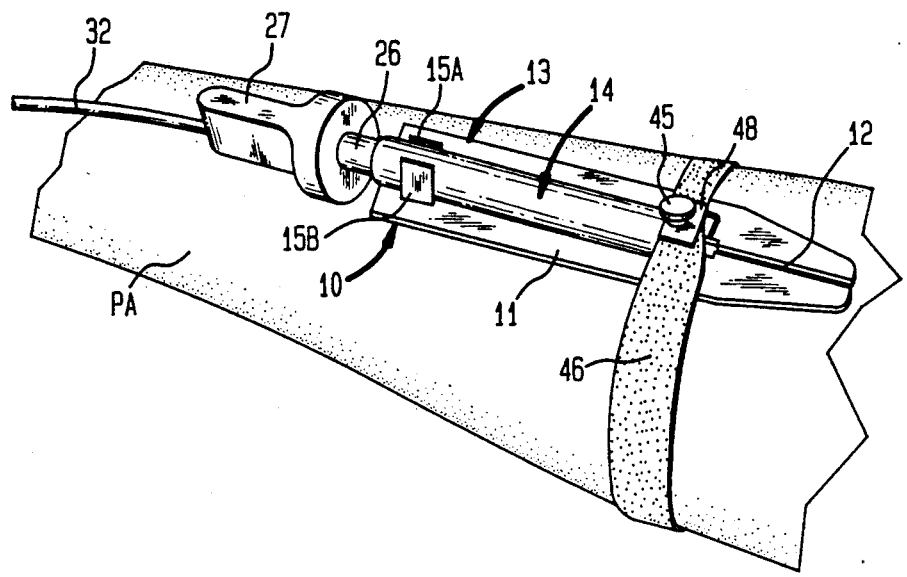
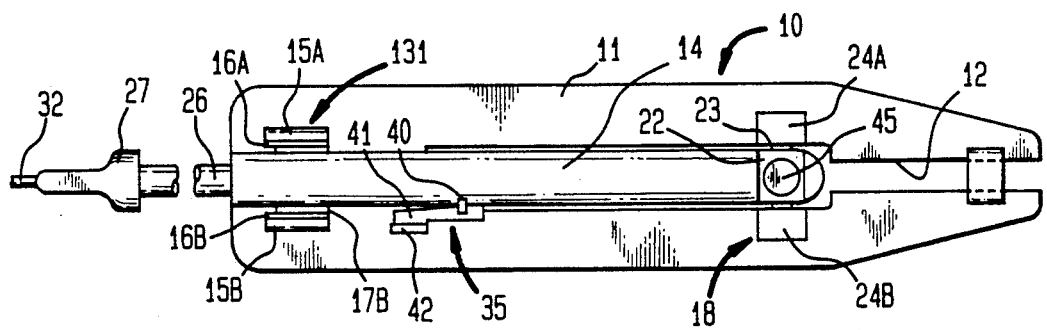
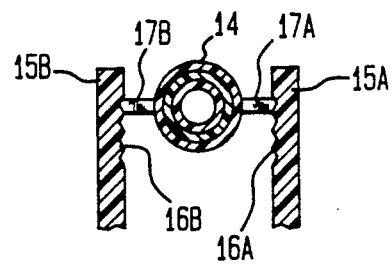
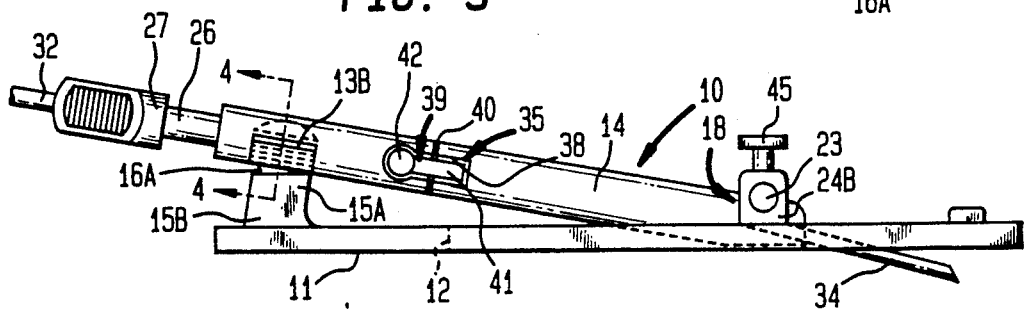

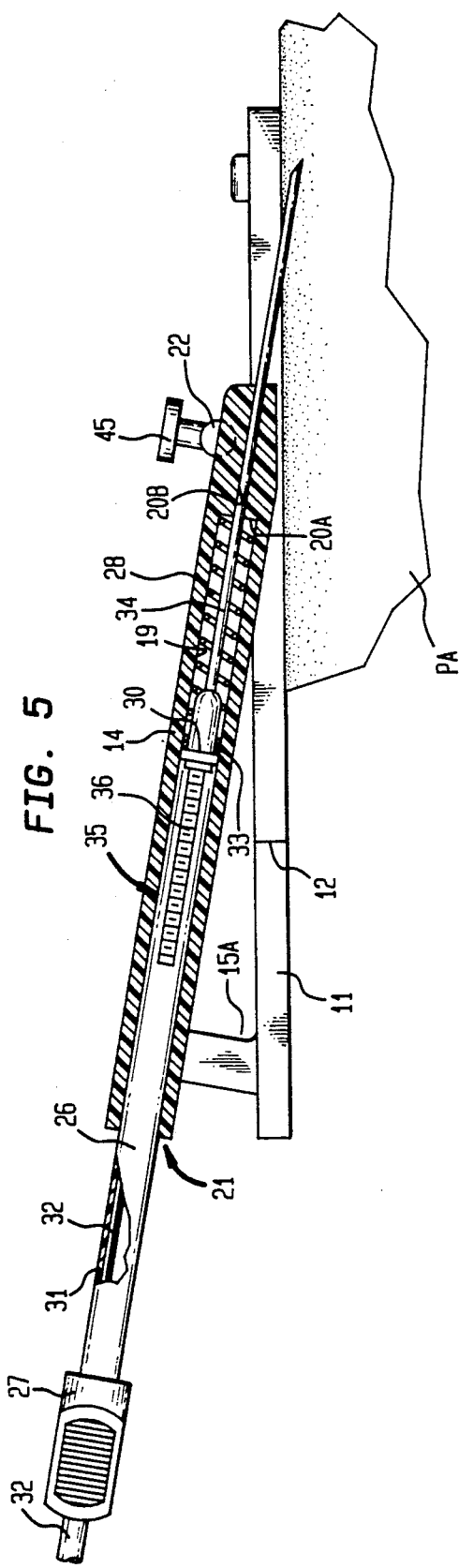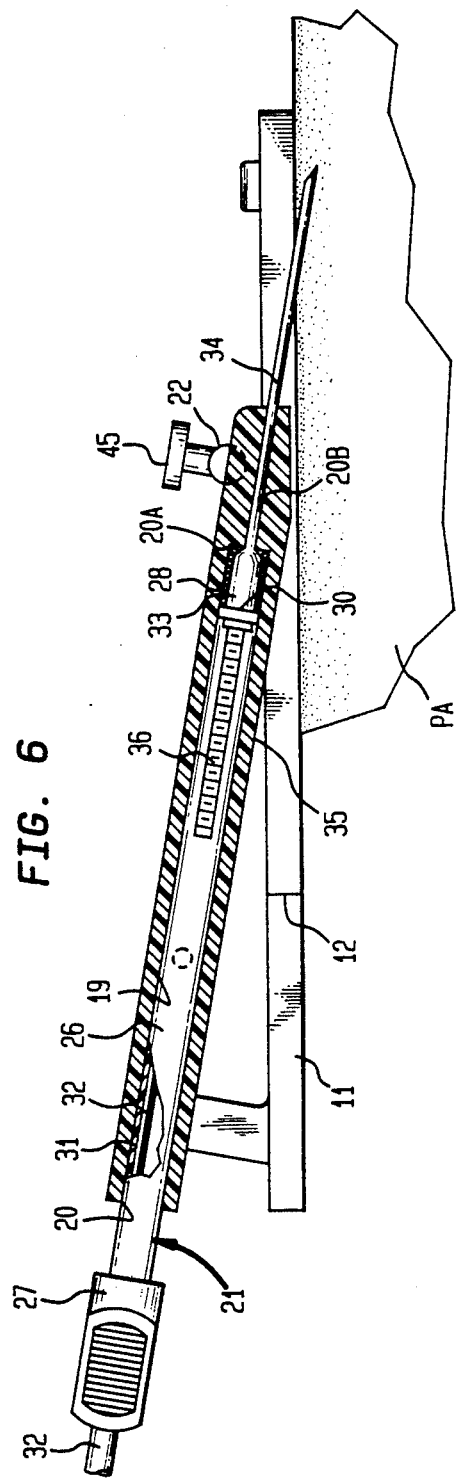

COMPOSITE CATHETER ASSEMBLY

This is a continuation of application Ser. No. 07/271,587, filed Nov. 14, 1988.

BACKGROUND OF THE INVENTION

This invention relates generally to devices for locating, inserting, and holding catheters to be implanted in patients and, more particularly, to a Composite Catheter Assembly for fixing, locating, inserting, and accurately securing intravenous catheters within body fluid-carrying conduits, preimplanted grafts, and the like in patients, and for the controlled retracting of such catheters from the inserted position in such body fluid-carrying conduits under safe, reliable, and aseptic conditions.

When used herein "catheter" is intended to include an intravenous catheter having a combination of elements for passing fluid to or from a fluid carrying conduit or blood vessel in a patient. Such intravenous catheters generally include a tubular conduit having a first connector at one end for connecting the tubular conduit to a source of enteral fluid for delivery to the patient or a reservoir for receiving fluid from the patient and a second connector at the end opposite from the first connector, and an elongated hollow needle having a head end for fixedly or removably connecting the needle to the second connector and a pointed end for inserting the needle into the fluid carrying conduit or blood vessel of the patient.

In the medical field the intravenous insertion of catheters, cannulas and the like into a patient generally require some means to secure the catheter or cannula in place for the period of use. This has generally been done by positioning a gauze pad and/or by the application of strips of tape for securing the catheter and associated tubing to the patient so as to prevent any accidental removal of the catheter by sudden or accidental movements of the patient. This technique is not acceptable because the placement of the catheters or cannulas is entirely non-uniform and becomes a hit or miss proposition so that proper placement of the catheter is clearly not insured. Further, such placement is quite slow and is dependent upon the ability of the nurse or other technician who is applying the catheter or cannulas to the patient.

Furthermore, the handling of needles, catheters and cannulas by nurses and other medical personnel has posed a serious problem in today's society with the onset of infectious diseases and with the problem of AIDS. Medical personnel have been known to contract the disease AIDS and other infectious diseases by accidentally pricking themselves with needles used for insertion into patients either upon taking the needle out or at times putting the needles into the patient. There has thus been a continuing search for new devices to replace the present prior art type devices so as to insure proper application, and securing of the catheters, cannulas or other needle type devices inserted into the patient, and to protect the medical personnel from accidental contact with various infectious diseases and, in particular, the AIDS virus.

The prior art has, in this crowded art, developed many devices seeking to accomplish this desirable end such as those shown in U.S. Pat. Nos. 2,402,306; 3,021,842; 3,288,137; 3,900,026; 4,170,993; 4,316,461; and 4,332,248.

In particular, for example U.S. Pat. No. 4,170,993 to Alvarez discloses a sliding intravenous needle carrier assembly which includes, a delta-shaped base plate with an open ended barrel secured to the base plate. An intravenous needle carrier is slidingly received within the barrel. The carrier is provided with a manually movable lateral projection which extends through a slot in the barrel so that the carrier with the needle can be manually moved between its forward position until the lateral projection falls into a forward detent so that the needle is fully extended through the front open end of the barrel; and its rearward retracted position in which the lateral projection falls into a rear detent and the needle is completely retracted in the barrel. Rotating the grasping projection of the needle carrier in the detent locks the needle carrier in either the rearward or forward position. The base plate is anchored to the patient's skin by means of adhesive strips after the needle is inserted into the blood vessel.

There is no adjustable angular positioning mechanism in the Alvarez patented device to insure appropriate angular entry of the needle, nor is there any non-contracting mechanism for retracting the needle to protect medical personnel from direct contact with the pointed end of the needle on the catheter. In addition, the anchoring means of U.S. Pat. 4,170,933 is affixed to the patient after insertion of the needle.

The prior art also discloses angular entry of the catheter as disclosed in U.S. Pat. No. 2,402,306 to Turkel. This patent includes, an anchoring or base support for the catheter with side extending leaf members which can be attached by tape or the like to the patient. The support includes means for angular entry of the needle and in the embodiment shown in FIGS. 4, 5, 9 and 10, thereof, there is a provision for altering the angle of the needle. However, as in the other prior art devices, it still becomes necessary to try to carefully aim the catheter into the desired injection site and no physical means are provided for insuring that the catheter is properly placed and aligned with the preimplanted graft or the like.

The search, therefore, continues for a practical device which can accurately and securely assist in fixing the intravenous catheter in place, not only by permitting insertion at precisely the right location, angle and depth, but which can also firmly secure the catheter in place without additional difficulty and will protect the nurse or other medical personnel from contact with body fluid that may remain in the exposed needle when the intravenous catheter is retracted and removed.

The present invention provides an improved Composite Catheter Assembly for meeting and overcoming these problems of the prior art wherein an anchoring or attachment plate with an elongated longitudinal opening thereon can be aligned and affixed to the patient at the site of a fluid carrying conduit, a barrel member is pivotally connected to the attachment plate in the longitudinal line of the elongated opening had has a bore extending inwardly from one end of the barrel at least a portion of length of said barrel to form an opening at the end thereof and a transverse shoulder at the opposite end to permit a sized opening to be formed in that end of the barrel so that the bore communicates with the exterior of the barrel, and a catheter slidably mounted in the bore of the barrel for movement from a retracted position to an extended position in which the needle end of the catheter will extend through the sized opening in the barrel and project past the longitudinal opening in the attachment plate for accurate insertion into the fluid carrying conduit of the patient, the catheter assembly including, a latch assembly having, a resilient member which is compressed when the catheter is moved to the extended position, and a locking means having a release lever pivotally connected to the barrel and operative to hold the catheter in the extended position and adapted on manual movement so that the resilient member can retract the catheter and withdraw the entire needle safely into the bore of the barrel.

SUMMARY AND OBJECTS OF THE INVENTION

Thus, the present invention covers a Composite Catheter Assembly for inserting and removing an intravenous catheter having needle means into and out of a fluid carrying conduit of a patient which includes, an attachment plate to be connected to the patient at the sight of the fluid carrying conduit, a barrel member having, a bore therein open at one end and having a transverse shoulder with a sized opening therein at the opposite end, is pivotally connected to the attachment plate to fix the angular position of the barrel with respect to the attachment plate, whereby the catheter can be slidably mounted in the bore of the barrel for movement of the needle on the catheter from a retracted position in the bore to an extended position into the fluid carrying conduit in the patient, and a latch assembly operatively associated with the catheter for non-contacting retraction of the hollow needle of the catheter into the barrel from the extended position.

In accordance with another embodiment of the present invention as above described, the attachment plate is provided with an elongated longitudinal opening extended inwardly from one end disposed in alignment with the fluid carrying conduit when the attachment plate is connected to the patient, and the barrel member is pivotally connected to the attachment plate at a point transversely of the longitudinal opening inwardly from the end of the attachment plate so that on movement of the needle of the catheter to the extended position the needle will extend through the opening in the barrel and project through the longitudinal opening on the attachment plate for accurate insertion into the fluid carrying conduit in the patient.

In accordance with another embodiment of the present invention as above described the attachment plate is provided with a bracket means having spaced uprightly extending arms disposed on opposite sides of the barrel member, the uprightly extending arms having aligned splines on the oppositely facing inner walls thereof so that lateral projections on the barrel member can be fitted into any one of said pair of aligned splines to fix the angular position of the barrel member relative to the attachment plate.

In accordance with another embodiment of the present invention as above described, the catheter includes, an elongated carrier which has a portion thereof slidably mounted for movement to and from in the bore of the barrel member, the carrier has a handle member at the exterior end to permit manual movement of the catheter from a retracted position where the needle is in the bore of the barrel member to an extended position into the fluid carrying conduit of the patient.

In accordance with still another embodiment of the present invention as above described, the catheter assembly includes, a latch means having a resilient member in the bore of the barrel which is compressed on movement of the catheter from the retracted position to the extended position, and a locking which holds and locks the catheter assembly in the extended position and has a manually operated pivotally mounted release lever to release the catheter so that the compressed resilient member can act to return the catheter to the retracted position and thus withdraw the needle back into the bore of the barrel member.

In accordance with still another embodiment of the present invention as above described, the latch means for locking and holding the catheter in the extended position and for releasing the catheter from the extended position for return to the retracted position includes an elongated ratchet member having unidirectional teeth thereon connected to the side of the carrier member, and a release lever pivotally mounted on the associated side of the barrel member has an inwardly directed projecting member normally operable to engage the teeth of the ratchet member when the catheter is moved to the extended position to lock the catheter in the extended position until the release lever is manually actuated to release the catheter for movement back to the retracted position.

Accordingly, it is an object of the present invention to provide an improved Composite Catheter Assembly which can be securely attached to a patient at the site of a fluid carrying conduit so that a catheter can be accurately extended for insertion into the fluid carrying conduit and can be actuated to return to a retracted position so that the needle of the catheter is safely withdrawn into a suitable protective member.

It is another object of the present invention to provide an improved Composite Catheter Assembly which can be operated manually for automatic retraction of the catheter so as to provide non-contacting withdrawal of the needle of the catheter in the use thereof.

Other and additional objects of the present invention will be more fully appreciated and understood with reference to the detailed description and claims set forth hereinafter with reference to the drawings as follows:

BRIEF DESCRIPTION OF THE DRAWINGS

FIG. 1 is a perspective view of one form of the Composite Catheter Assembly and catheter in accordance with the present invention affixed to the arm of a patient.

FIG. 2 is a top plan view of the Composite Catheter Assembly as shown in FIG. 1 of the drawings.

FIG. 3 is a side elevational view of the Composite Catheter Assembly as shown in FIGS. 1 and 2 of the drawings with one of the arms of the bracket for controlling angular elevation of the intravenous catheter broken away.

FIG. 4 is a cross section taken on line 4—4 of FIG. 3.

FIG. 5 is a cross section taken on line 5—5 of FIG. 2 showing the needle in the retracted position.

FIG. 6 is the same cross section as FIG. 5 showing the intravenous catheter in the extended or inserted position.

DESCRIPTION OF ONE PREFERRED EMBODIMENT OF THE INVENTION

Figure 7:
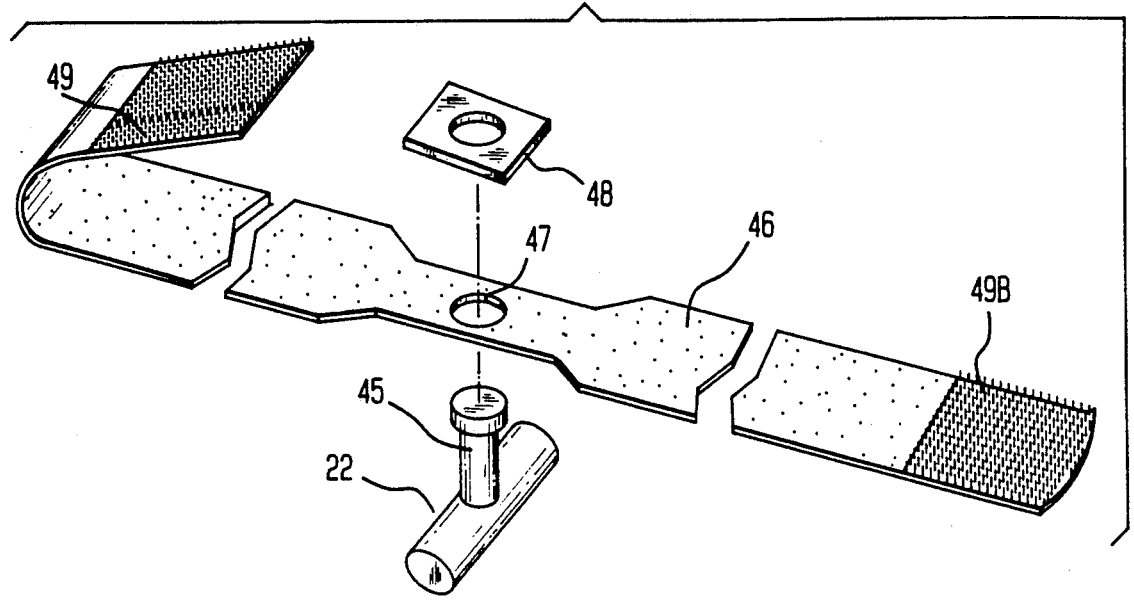
FIG. 7 is an exploded view of one form of strap assembly for fastening the attachment plate to the patient.
Figure 8:
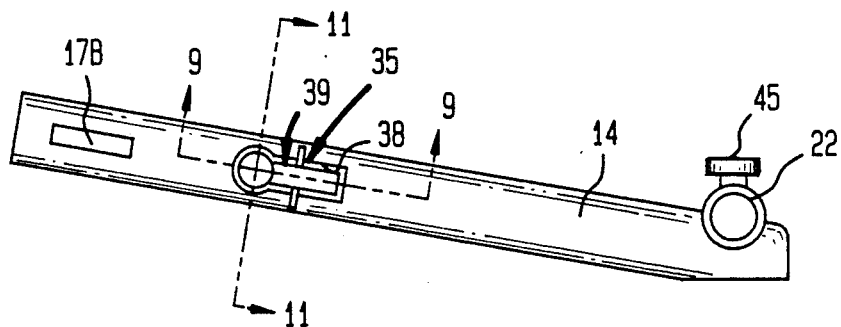
FIG. 8 is a side elevational view of the barrel member of the Composite Catheter Assembly in accordance with the present invention.

Referring to the drawings in FIGS. 1 to 4 one preferred form of the Composite Catheter Assembly in accordance with the present invention generally designated 10 for locating and inserting an intravenous catheter is shown attached to a patient's arm generally designated PA.

Composite catheter assembly 10 has an attachment or base plate 11 which is a generally elongated flat member made of a material that is sufficiently sturdy but smooth and flexible enough to be fitted comfortably against the skin surface of the patient where the fluid-carrying conduit is located. Thus, the attachment plate 11 may be made of a material such as an inert plastic like polypropylene, acrylonitrile-butadiene-styrene, polycarbonate, and the like which are sold on the open market. In the illustrated form of the present invention, the base attachment is shown as affixed to the arm of the patient which makes its readily accessible to any of a plurality of fluid-conducting conduits in the patient's arm as is well known to those skilled in the art.

While reference is made to the attachment plate as being made from a plastic material, those skilled in the art will readily recognize that the base attachment plate can be made of other more durable materials such as stainless steel, provided that the thickness and quality of material used is such that it can be adapted to fit on and be connected to the patient for the purposes and objects of the present invention.

Attachment plate 11 has an elongated opening as at 12 which extends inwardly from one end of the base attachment plate as is clearly shown in FIGS. 1, 2 and 3 of the drawings.

On the end of the base attachment plate remote from the inwardly extending opening 12, a bracket member 13 is formed for adjusting the elevation of a barrel member 14 for purposes that will be clear from the description of the operation of the present device as will be set forth below.

Bracket member 13 includes a pair of spaced retaining arms 15a and 15b which are disposed respectively on opposite sides of the barrel member 14. The retaining arms 15a and 15b each respectively include on the innermost surface a plurality of serially disposed inwardly facing teeth or splines as at 16a on retaining arm 15a and 16b on retaining arm 15b. The barrel member 14 has operatively associated side projections on opposite sides as at 17a and 17b which are disposed to engage the associated teeth or splines 16a and 16b on the same sides of the barrel member as the side projection 17a and 17b, all of which is shown in FIGS. 1, 2, 3 and 4 of the drawings.

The retaining arms are also made of plastic and will be sufficiently resilient so that the barrel member can be manually moved to adjust the relative elevation thereof with respect to the opposite end of the barrel member which is pivotally connected as at 18 to the base attachment plate at a point inwardly of the end thereof opposite from the end having the bracket 13 thereon as is also shown in FIGS. 1, 2, 3, and 4 of the drawings.

Referring next to FIGS. 5 and 6, barrel 14 is a cylindrical member which has an inwardly extending longitudinal bore 19 which extends a portion of the length of the barrel. Bore 19 is open at one end of the barrel as at 20 and at the opposite end forms a transverse shoulder 20a which has a sized opening 20b opening to the exterior of the barrel member 14. Bore 19 is so sized that an intravenous catheter generally designated 21 can be inserted therein and will have a sliding fit with the wall of the barrel member 14 defining the bore 19. Further, at the end of the barrel member opposite from the opening 20, the barrel member is provided with an annular housing as at 22 in which an axle 23 is fixedly connected so that the axle 23 can extend laterally on opposite sides of the barrel for pivotally mounting the barrel member in spaced journals as at 24a and 24b on the attachment plate 11. The relatively small passage or sized opening 20b at the pivotally mounted end of the barrel member communicates with the bore 19 and provides a passage for the needle end of the intravenous catheter 21 which is slidably mounted in the bore 19 for movement from a retracted position when the needle member is in the bore 19 of the barrel member 14, to an extended position in which the needle is designed to extend through the sized opening 20b all of which is clearly shown in FIGS. 2, 3, 5, and 6 of the drawings.

FIGS. 2 and 3 further show that the pivoted end of the barrel member 14 is so operatively associated with the elongated opening 12 in the attachment plate 11 that the passage or sized opening 20b is positioned to permit the needle member of the catheter 20 to be extended as, for example, as shown in FIG. 3 and 6 of the drawings, to easily fit and extend through the elongated opening 12, to facilitate the function and use of the attachment plate for the Composite Catheter Assembly 10 in accordance with the present invention.

The catheter as shown in this form of the invention includes a hollow elongated carrier 26 whose outer diameter is sized to permit a sliding fit with the inner wall of the bore 19 of the barrel member 14. Carrier member 26 at the portion thereof which is disposed exteriorly of the barrel when the carrier 26 is in position in bore 19, is provided with a knob 27 which enables the carrier to be manually pressed or forced into the bore 19 against a spring member 28 disposed in the bore 19 about the needle end of the catheter 21 between the transverse shoulder 20a at the inner end of the bore 19 and the end 30 of carrier 26 so that when the carrier 26 is pushed inwardly under manual force, the spring 28 will be compressed, all of which is shown in FIGS. 5 and 6 of the drawings.

The intravenous catheter includes an inner passage 31 extending along the longitudinal line of the carrier 26 and includes a connector portion 33 and fixedly or detachably connected to connector portion 33 is the hollow needle 34 of conventional form as will be understood by those skilled in the art. Needle 34 is sized so that in the retracted position as shown in FIG. 5 the needle will lie within the barrel member 14. As carrier member 26 is pushed inwardly under manual force the needle 34 will extend to the exterior of the barrel member 14 through the size opening 20b and through the opening 12 in the attachment plate 11 so that it can be introduced into the fluid-carrying conduit in the patient's body, as is illustrated in FIGS. 5 and 6 of the drawings.

In order to prevent the composite catheter assembly from retracting needle 34 until it is necessary to do so the composite catheter assembly in accordance with the present invention is provided with a latch and locking device generally designated 35. The latch and locking assembly cooperates with a ratchet member 36 which is fixedly connected to the outside of the carrier 26 either by being formed therewith and/or by being adhesively or otherwise connected to the outer surface thereof so that it is in a position to move along the longitudinal line of the barrel 14. Barrel 14 is provided with an opening as at 38 in which a latch 39 is pivotally connected as at 40. The latch 39 being disposed for pivotal and operative engagement with the ratchet member 36 so as to engage the same and thus prevent backward or retracting action of the carrier 26 after the needle 34 is inserted into assembled position in the fluid-carrying conduit in the patient. For this purpose, latch member 39 has an elongated lever arm 41 having a manual button 42 at one end and an inwardly extending projection 42 at the end opposite therefrom which is normally disposed for engagement with the ratchet member 36 when the carrier is pushed forward to compress the spring 28 as shown in FIG. 6 of the drawings. When it is desired to release the carrier 26 and cause the carrier and intravenous catheter to move to the retracted position, the manual button 42 is depressed so as to release the ratchet 36 and expansion of the spring 28 will move the catheter 21 to the retracted position where the needle 34 is withdrawn from the fluid-carrying conduit in the patient and pulled into a concealed position inside the chamber 19 thus providing safety and protection to any of the technical personnel using the composite catheter assembly in accordance with the present invention.

Figure 9:
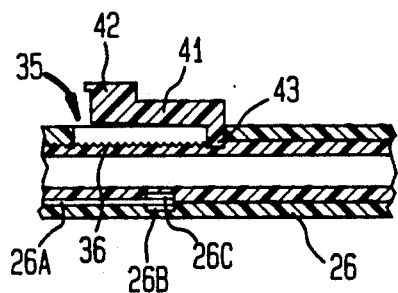
FIG. 9 is a fragmentary longitudinal cross section taken on line 9—9 of FIG. 8.
Figure 10:
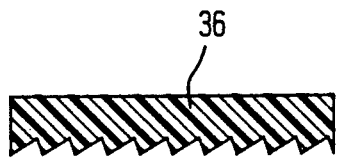
FIG. 10 is an enlarged fragmentary view of the ratchet teeth as shown in FIG. 9 of the drawings.
Figure 11:
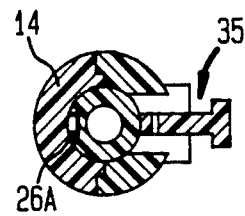
FIG. 11 is a transverse cross section taken on line 11—11 of FIG. 8.

FIG. 9 shows that the outer surface of the carrier 26 has a longitudinally extruding groove 26a on the side opposite from the latch and locking assembly which defines a stop shoulder 26b. This groove 26a and stop shoulder 26b coact with a stop member 26c which is formed by a set screw threadably connected in the side of the barrel member so that it will ride in the groove 26a and engage the stop shoulder 26b to prevent the retracting force exerted by spring 28 from pushing the carrier 26 and the catheter 21 from the bore 19 in the barrel member 14.

In order to securely connect the attachment plate in assembled position on the patient, a strap retaining stud as at 45 is provided on the upper portion of the annular housing 22. A shaped strap member 46 made of any suitable material such as a urethane foam is provided with a reinforced eyelet as at 47 to connect the strap member 46 into assembled position on the strap retaining stud 45 and a locking plate 48 is also affixed onto the strap retaining stud 45 to hold, support and strengthen the strap member 46 in assembled position. At the respective opposite ends of the strap member 46 a velcro connector as at 49a and 49b is provided so that the strap member 46 can be overlapped sufficiently to provide the desired snug engagement of the attachment plate 11 to the patient as for example in the manner illustrated at FIG. 1 and as shown in FIG. 7 of the drawings.

While this form of attaching means is illustrated those skilled in the art will readily recognize that the strap can be made with a suitable buckle or any other suitable connecting mechanism can be provided for this purpose without departing from the scope of the present invention.

Thus, a preferred form of Composite Catheter Assembly has been shown and described for achieving the desired advantageous object and purpose of the present invention.

This Composite Catheter Assembly because of the structure and arrangement for retracting the contaminated needle end of the catheter back into the barrel provides a clearly defined safety device against the dangers involved in treating patients with AIDS, Hepatitis, and Cancer. Further, however, it is desirable and useful in areas where the needle of the catheter assembly must be securely held "in situ" in the patient's fluid carrying conduit such as a blood vessel for lengthy periods of time, such as during Anaesthesiology, T.P.N.—Total Parenteral Nutrition, and during the transport of wounded soldiers out of a battlefield zone or from a field hospital.

Where the Composite Catheter Assembly in accordance with the present invention is being used as a safety device, it will be made of materials which permit the entire Composite Catheter Assembly to be disposed of or destroyed to further protect those persons who must treat or come in contact with the deadly contaminants and virus which infect AIDS, Hepatitis, and Cancer victims.

It will be understood that the invention is not to be limited to the specific construction or arrangement of parts shown but that they may be widely modified within the invention defined by the Claims.

What is claimed is:

1. A composite catheter assembly for inserting and removing an intravenous catheter including needle means and a ratchet member in a fluid-carrying conduit of a patient, said composite catheter assembly comprising a barrel member having an inner chamber for slidably accommodating said intravenous catheter, whereby said needle means may be maintained in a retracted position entirely within said barrel member and slidably moved from said retracted position entirely within said barrel member into an extended position into said fluid-carrying conduit of said patient, retraction means comprising a resilient assembly for operatively retracting and returning said needle means into said barrel member from said extended position to said retracted position, and latch means operatively associated with said resilient assembly for actuating said intravenous catheter to move said needle means from said extended position to said retracted position, said latch means including pivotally mounted lever means on said barrel member disposed for releasable engagement with said ratchet member on said intravenous catheter when said needle means is moved to said extended position to releasably lock said needle means in said extended position.

2. The combination of an intravenous catheter including needle means and a composite catheter assembly for inserting and removing said needle means into a fluid-carrying conduit of a patient, said composite catheter assembly comprising a barrel member having a bore therein and having a first end and a second end and being open at said first end whereby said needle means may be moved from a retracted position in said barrel member to an extended position into the fluid-carrying conduit of the patient, retraction means comprising a generally resilient member disposed about said intravenous catheter for operatively retracting and returning said needle means on said intravenous catheter into said barrel member from said extended position, whereby on movement of said needle means from said retracted position to said extended position said resilient means is compressed, latch means operatively associated with said resilient means for releasing said compressed resilient member to actuate said needle means to move from said extended position to said retracted position, said latch means including an elongated ratchet member on the side of a portion of said intravenous catheter disposed in said barrel member, and pivotally mounted lever means on said barrel member disposed for releasable engagement with said ratchet member when said needle means is moved to said extended position to releasably lock said needle means in said extended position.

3. A combination as claimed in claim 2 wherein said intravenous catheter includes elongated carrier means, and wherein said elongated carrier means extends from said needle means and projects from said inner chamber.

4. A combination as claimed in claim 3 wherein said elongated carrier means includes a handle member, whereby said intravenous catheter may be manually moved by means of said handle member from said retracted position to said extended position.

5. The combination of an intravenous catheter including an elongated carrier and needle means and a composite catheter assembly for inserting and removing said needle means in a fluid-carrying conduit of a patient, said composite catheter assembly comprising a barrel member having an inner chamber for slidably accommodating said intravenous catheter, whereby said needle means may be maintained in a retracted position entirely within said barrel member and slidably moved from said retracted position entirely within said barrel member into an extended position into said fluid-carrying conduit of said patient, said elongated carrier extending from said barrel member and being slidably movable therein, and retraction means comprising a resilient assembly for operatively retracting and returning said needle means into said barrel means from said extended position to said retracted position.

6. A combination as claimed in claim 5 including latch means operatively associated with said resilient assembly for actuating said needle means to move from said extended position to said retracted position.

7. A combination as claimed in claim 6 wherein said latch means includes an elongated ratchet member on the side of the portion of said elongated carrier disposed in said barrel member and pivotally mounted lever means on said barrel member disposed for releasable engagement with said ratchet member when said intravenous catheter is moved to said extended position to releasably lock said catheter in said extended position.

8. A combination as claimed in claim 5 including conduit means operatively connected to said elongated carrier whereby said conduit means is fluidly connected to said elongated carrier and said needle means can thereby remain in said fluid-carrying conduit and provide continuous fluid access though said conduit means thereto.

9. A combination as claimed in claim 5 including platform mounting means whereby said composite catheter assembly can be mounted on said patient.

10. A composite catheter assembly as claimed in claim 5 wherein said carrier means includes a handle member, whereby said catheter assembly may be manually moved by means of said handle member from said retracted position to said extended position.

11. A composite catheter assembly as claimed in claim 10 including conduit means operatively connected to said elongated carrier means whereby said conduit means is fluidly connected to said elongated carrier means and said needle means and said catheter assembly can thereby remain in said fluid-carrying conduit and provide continuous fluid access through said conduit means.

* * * * *

UNITED STATES PATENT AND TRADEMARK OFFICE
CERTIFICATE OF CORRECTION

PATENT NO. : 5,024,665

DATED : June 18, 1991

INVENTOR(S) : Jerry M. Kaufman

It is certified that error appears in the above-identified patent and that said Letters Patent is hereby corrected as shown below:

Column 2, line 58, "had" should read --and--.

Column 10, line 16, "though" should read --through--.

Signed and Sealed this

Seventeenth Day of November, 1992

Attest:

DOUGLAS B. COMER

*Attesting Officer*      *Acting Commissioner of Patents and Trademarks*